US00PP26940P2

(12) United States Plant Patent
Dummen

(10) Patent No.: US PP26,940 P2
(45) Date of Patent: Jul. 12, 2016

(54) ***PELARGONIUM* PLANT NAMED 'DUEVOREILAC'**

(50) Latin Name: ***Pelargonium zonale*×*Pelargonium peltatum***
Varietal Denomination: Duevoreilac

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 157 days.

(21) Appl. No.: 14/120,832

(22) Filed: Jul. 1, 2014

(51) Int. Cl.
*A01H 5/02* (2006.01)

(52) U.S. Cl.
USPC ..... Plt./329

(58) Field of Classification Search
USPC ..... Plt./329
See application file for complete search history.

*Primary Examiner* — Keith Robinson
(74) *Attorney, Agent, or Firm* — C. A. Whealy

(57) ABSTRACT

A new and distinct cultivar of Interspecific Geranium plant named 'Duevoreilac', characterized by its upright to outwardly spreading and rounded plant habit; vigorous growth habit; freely basal branching habit; dark green-colored leaves; freely flowering habit; large red purple-colored flowers; and good garden performance.

1 Drawing Sheet

Botanical designation: *Pelargonium zonale*×*Pelargonium peltatum.*

Cultivar denomination: 'DUEVOREILAC'.

BACKGROUND OF THE INVENTION

The present invention relates to a new and distinct cultivar of Interspecific Geranium plant, botanically known as *Pelargonium zonale*×*Pelargonium peltatum*, and hereinafter referred to by the name 'Duevoreilac'.

The new Interspecific Geranium plant is a product of a planned breeding program conducted by the Inventor in Rheinberg, Germany. The objective of the breeding program is to create new vigorous double-flowered Geranium plants with dark-colored leaves and numerous attractive flowers.

The new Interspecific Geranium plant originated from a cross-pollination made by the Inventor in July, 2010 in Rheinberg, Germany of a proprietary selection of *Pelargonium zonale* identified as code number F-0304-018, not patented, as the female, or seed, parent with a proprietary selection of *Pelargonium peltatum* identified as code number G09-0403-003, not patented, as the male, or pollen, parent. The new Interspecific Geranium plant was discovered and selected by the Inventor as a single flowering plant from within the progeny of the stated cross-pollination in a controlled greenhouse environment in Rheinberg, Germany in May, 2012.

Asexual reproduction of the new Interspecific Geranium plant by vegetative terminal cuttings in a controlled greenhouse environment in Rheinberg, Germany since June, 2012 has shown that the unique features of this new Interspecific Geranium plant are stable and reproduced true to type in successive generations.

SUMMARY OF THE INVENTION

Plants of the new Interspecific Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duevoreilac'. These characteristics in combination distinguish 'Duevoreilac' as a new and distinct Interspecific Geranium plant:

1. Upright to outwardly spreading and rounded plant habit.
2. Vigorous growth habit.
3. Freely basal branching habit.
4. Dark green-colored leaves.
5. Freely flowering habit.
6. Large red purple-colored flowers.
7. Good garden performance.

Plants of the new Interspecific Geranium differ primarily from plants of the female parent selection in flower color as plants of the female parent selection have red-colored flowers. In addition, plants of the new Interspecific Geranium are more compact than plants of the female parent selection.

Plants of the new Interspecific Geranium differ primarily from plants of the male parent selection in flower color as plants of the male parent selection have hot pink-colored flowers. In addition, plants of the new Interspecific Geranium are more vigorous than plants of the male parent selection.

Plants of the new Interspecific Geranium can be compared to plants of the Interspecific Geranium 'Calliope Lavender', not patented. In side-by-side comparisons conducted in Rheinberg, Germany, plants of the new Interspecific Geranium differed primarily from plants of 'Calliope Lavender' in the following characteristics:

1. Plants of the new Interspecific Geranium were more compact than plants of 'Calliope Lavender'.
2. Leaves of plants of the new Interspecific Geranium had a discernible zonation pattern whereas leaves of plants of 'Calliope Lavender' did not have a discernible zonation pattern.
3. Plants of the new Interspecific Geranium and 'Calliope Lavender' differed slightly in flower color.

BRIEF DESCRIPTION OF THE PHOTOGRAPH

The accompanying colored photograph illustrates the overall appearance of the new Interspecific Geranium plant showing the colors as true as it is reasonably possible to obtain in colored reproductions of this type. Colors in the photograph may differ slightly from the color values cited in the detailed botanical description which accurately describe the colors of the new Interspecific Geranium plant.

The photograph comprises a side perspective view of a typical flowering plant of 'Duevoreilac' grown in a container.

DETAILED BOTANICAL DESCRIPTION

The aforementioned photograph and following observations and measurements describe plants grown during the summer in 12-cm containers in a glass-covered greenhouse in Rheinberg, Germany and under cultural practices typical of commercial *Pelargonium* production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 2007 Edition, except where general terms of ordinary dictionary significance are used.

Botanical classification: *Pelargonium zonale*×*Pelargonium peltatum* 'Duevoreilac'.

Parentage:

*Female, or seed, parent*.—Proprietary selection of *Pelargonium zonale* identified as code number F-0304-018, not patented.

*Male or pollen parent*.—Proprietary selection of *Pelargonium zonale* identified as code number G09-0403-003, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous.

*Rooting habit*.—Freely branching; dense.

Plant description:

*Plant and growth habit*.—Upright to outwardly spreading plant habit; uniformly rounded; densely foliated; vigorous growth habit.

*Branching habit*.—Freely basal branching habit with about seven basal branches developing per plant.

*Plant height to top of flower umbels*.—About 31 cm.

*Plant height to top of foliar plane*.—About 22 cm.

*Plant width*.—About 64 cm.

*Lateral branches*.—Length: About 18 cm. Diameter: About 7 mm. Internode length: About 2.5 cm. Texture: Pubescent. Strength: Moderately strong. Color: Close to 144A.

Leaf description:

*Arrangement*.—Alternate; simple.

*Length*.—About 3.8 cm.

*Width*.—About 6.3 cm.

*Shape*.—Roughly reniform.

*Apex*.—Acute.

*Base*.—Cordate.

*Margin*.—Crenate.

*Venation pattern*.—Palmate.

*Texture, upper surface*.—Pubescent.

*Texture, lower surface*.—Smooth, glabrous.

*Color*.—Developing leaves, upper surface: Close to N137A. Developing leaves, lower surface: Close to 146A. Fully expanded leaves, upper surface; Close to N137A to N137B; venation, close to N137B. Fully expanded leaves, lower surface; Close to 146A; venation, close to 146C.

*Zonation pattern*.—Distance from margin: About 1.3 cm. Width: About 2 cm. Color: Close to 137B.

*Petioles*.—Length: About 4.9 cm. Diameter: About 1.4 mm. Texture, upper and lower surfaces: Smooth, glabrous. Color, upper surface: Close to 146B. Color, lower surface: Close to 146C.

Flower description:

*Flower arrangement*.—Semi-double type flowers arranged in rounded hemispherical umbels arising from apical leaf axils; umbels displayed above the foliar plane on moderately strong peduncles; flowers face mostly upright to outwardly.

*Fragrance*.—None detected.

*Flowering habit*.—Freely flowering habit, about seven to 21 flowers per umbel and about 50 flower umbels developing per plant.

*Flowering season*.—Year-round under greenhouse conditions; in outdoor nurseries and gardens in Germany, flowering is continuous from spring throughout the summer until the autumn; plants begin to flower about eight weeks after planting.

*Flower longevity*.—Individual flowers last about five to seven days on the plant; flowers persistent.

*Umbel height*.—About 4 cm.

*Umbel diameter*.—About 8 cm.

*Flower diameter*.—About 3.3 cm by 4.5 cm.

*Flower depth* (*height*).—About 1.9 cm.

*Flower buds*.—Length: About 1.3 cm. Diameter: About 8.2 mm. Shape: Ovoid. Color: Close to 67B.

*Petals*.—Quantity per flower: About five arranged in a single whorl. Length: About 2 cm. Width: About 1.5 cm. Shape: Obovate. Apex: Rounded. Base: Attenuate. Margin: Sinuate. Texture, upper and lower surfaces: Smooth, glabrous. Color: When opening, upper surface: Close to N74B. When opening, lower surface: Close to 64D. Fully opened, upper surface: Close to N74B; color becoming closer to 64A with development. Fully opened, lower surface: Close to N66C; color becoming close to 64C with development.

*Petaloids*.—Quantity per flower: About two. Length: About 1.4 cm. Width: About 5 mm. Shape: Obovate. Apex: Rounded. Base: Attenuate. Margin: Sinuate. Texture, upper and lower surfaces: Smooth, glabrous. Color: When opening and fully opened, upper surface: Close to N74B. When opening and fully opened, lower surface: Close to 64D.

*Sepals*.—Quantity per flower: Five arranged in a single whorl. Length: About 1 cm. Width: About 2.2 mm. Shape: Ensiform. Apex: Apiculate. Margin: Entire. Texture, upper and lower surfaces: Smooth, glabrous. Color, upper and lower surfaces: Close to 144A.

*Peduncles* (*umbel stems*).—Length: About 12.2 cm. Diameter: About 2.3 mm. Strength: Moderately strong. Texture: Smooth, glabrous. Color: Close to 146B.

*Pedicels* (*individual flower stems*).—Length: About 2.5 cm. Diameter: About 1.2 mm. Strength: Moderately strong. Texture: Smooth, glabrous. Color: Close to 148B and N199A.

*Reproductive organs*.—Androecium: Stamen quantity per flower: About five. Filament length: About 2.6 mm. Filament color: Close to 68D. Anther length: About 1.7 mm. Anther shape: Oblong. Anther color: Close to 167C. Pollen amount: Moderate. Pollen color: Close to 28A. Gynoecium: Pistil quantity per flower: One. Pistil length: About 2.5 mm. Stigma shape: Tapering. Stigma color: Close to 59A. Style length: About 2 mm. Style color: Close to 59C. Ovary color: Close to 143C.

*Seeds and fruits*.—Seed and fruit development have not been observed on plants of the new Interspecific Geranium.

Disease & pest resistance: Plants of the new Interspecific Geranium have not been observed to be resistant to pathogens and pests common to Interspecific Geranium plants.

Garden performance: Plants of the new Interspecific Geranium have been observed have good garden performance and to tolerate rain, wind, and temperatures ranging from about 5° C. to about 40° C.

It is claimed:

1. A new and distinct Interspecific Geranium plant named 'Duevoreilac' as illustrated and described.

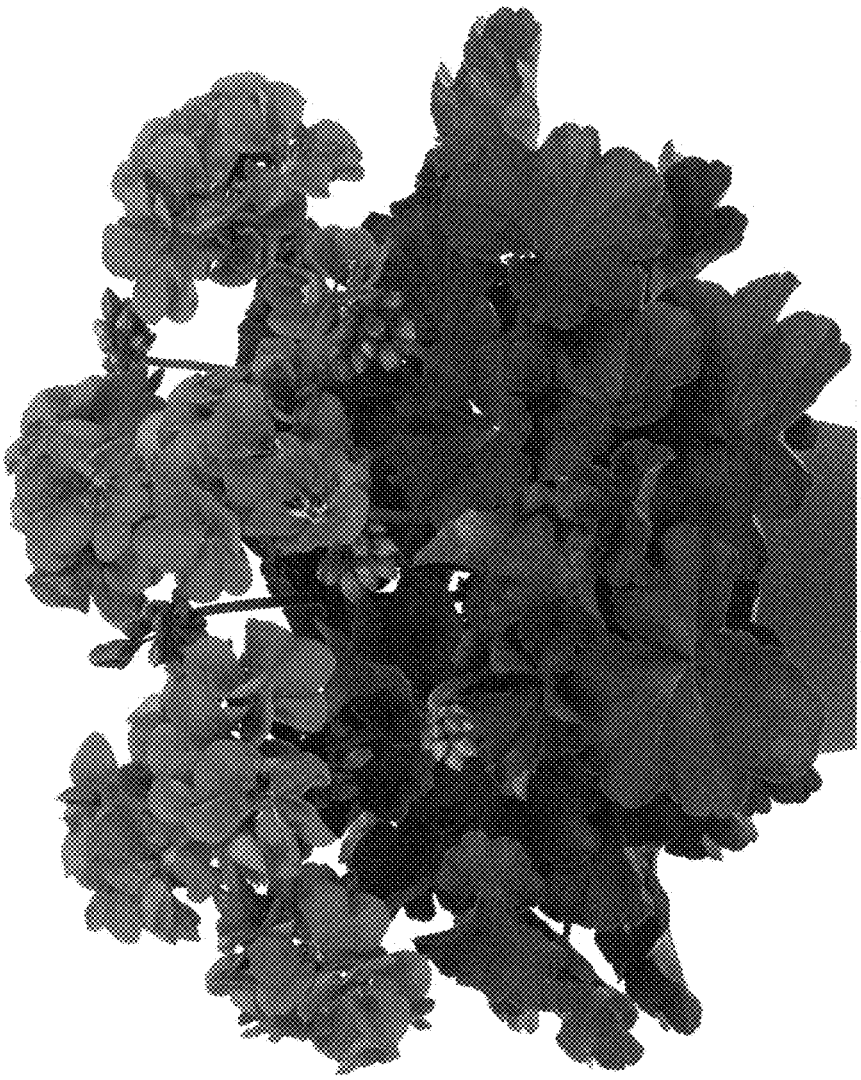

* * * * *